United States Patent [19]

Cheminal et al.

[11] Patent Number: 5,053,564
[45] Date of Patent: Oct. 1, 1991

[54] SELECTIVE HYDROGENOLYSIS OF PERHALOGENATED ETHANE DERIVATIVES

[75] Inventors: Bernard Cheminal, Brignais; Jean-Marie Cognion; Dominique Guillet, both of Saint-Genis Laval, all of France

[73] Assignee: Societe Atochem, Puteaux, France

[21] Appl. No.: 453,997

[22] Filed: Dec. 20, 1989

[30] Foreign Application Priority Data

Jan. 19, 1989 [FR] France .................................. 89 00601

[51] Int. Cl.$^5$ .............................................. C07C 19/08
[52] U.S. Cl. .................................................... 570/176
[58] Field of Search .......................................... 570/176

[56] References Cited

U.S. PATENT DOCUMENTS 3,636,173  1/1972  Gardner ............................... 570/176
4,873,381 10/1989  Kellner et al. ....................... 570/176

FOREIGN PATENT DOCUMENTS 1258631 10/1989  Japan .
1319440 12/1989  Japan .
1578933 11/1980  United Kingdom ................ 510/176

Primary Examiner—Alan Siegel
Attorney, Agent, or Firm—Morgan & Finnegan

[57] ABSTRACT

The invention relates to the manufacture of chlorofluoroethanes of formula $CF_3—CHF_xCl_{2-x}$, where x is equal to 0 or 1, by the catalytic hydrogenation of a perhaloethane of formula: $CF_3—CF_xCl_{3-x}$. The use of a ruthenium-based catalyst deposited on a support enables the selectivity to be improved.

9 Claims, No Drawings

SELECTIVE HYDROGENOLYSIS OF PERHALOGENATED ETHANE DERIVATIVES

FIELD OF THE INVENTION

The present invention relates to the manufacture of chlorofluoroethanes of formula:

$$CF_3\text{-}CHF_xCl_{2-x} \quad (I)$$

where x is equal to 0 or 1, by the catalytic hydrogenation of a perhaloethane of formula:

$$CF_3CF_xCl_{3-x} \quad (II)$$

BACKGROUND OF THE INVENTION

The two starting materials, included in formula (II), are 1,1,1-trichloro-2,2,2-trifluoroethane ($CF_3CCl_3$) and 1,1-dichloro-1,2,2,2-tetrafluoroethane ($CF_3CFCl_2$), in which the substitution of a chlorine atom by a hydrogen atom leads, respectively, to 1,1-dichloro-2,2,2-trifluoroethane ($CF_3CHCl_2$) and to 1-chloro-1,2,2,2-tetrafluoroethane ($CF_3CHFCl$).

The catalytic hydrogenation of the compounds (II) has already been described, but the selectivities for the product corresponding to the removal of a single chlorine atom are low. Thus, the hydrogenolysis of 1,1-dichloro-1,2,2,2-tetrafluoroethane at 280° C. on a catalyst containing 5% of a palladium on charcoal (British Patent No. 1,578,933) yields a product containing 70% of 1,1,1,2-tetrafluoroethane. Similar results are obtained by C. GERVASUTTI, et al., Fluorine Chemistry, 1, 1-20 (1981) on a catalyst containing 0.5% of palladium on charcoal. At 170° C., the hydrogenolysis of 1,1-dichloro-1,2,2,2-tetrafluoroethane leads to 76% of 1,1,1,2-tetrafluoroethane. To solve the problem of the removal of a single chlorine atom, it is necessary to resort, according to Japanese patent application No. 106,051/82 (publication JP 222038/83) to a chemical reduction with the zinc/ethanol system. Under the conditions described, the selectivity of the hydrogenolysis of 1,1,1-trichloro-2,2,2-trifluoroethane to 1,1-dichloro-2,2,2-trifluoroethane reaches 90%. However, this process has the drawback of using costly metallic zinc, and of yielding zinc chloride as a by-product which must be destroyed.

The preceding references are hereby incorporated by reference.

DETAILED DESCRIPTION OF THE INVENTION

It has now been found that the catalytic removal of a single chlorine atom is accomplished very selectively if a ruthenium-based catalyst is used.

The subject of the present invention is a process for preparing chlorofluoroethanes of formula (I) by the catalytic hydrogenation of a perhaloethane of formula (II), characterized in that a ruthenium-based catalyst deposited on a support is used.

In the catalyst used according to the invention, the ruthenium content can range from 0.1 to 10% by weight, but is preferably between 0.2 and 8%.

The nature of the support can be highly diverse. It is chosen, for example, from aluminas, aluminum fluoride and active charcoals. Charcoals having a specific surface area of between 200 and 1500 m²/g (preferably between 600 and 1200 m²/g), a high porosity (0.3 to 0.7 cm³/g) and a particle size compatible with a fixed-bed catalysis (1 to 10 mm) are preferred supports. These products are marketed in extruded or bead form by many companies.

The catalyst according to the invention may be prepared by impregnation of the support with an aqueous or organic solution of a ruthenium derivative, evaporation of the water or solvent and heat treatment to a temperature ranging from 200° to 600° C. (preferably 300° to 450° C.) and under a stream of hydrogen (preferably under a pressure of 1 to 5 bars) to liberate the ruthenium. The nature of the ruthenium derivative used is unimportant. It can be, for example, a chloride, a nitrate, a chlororuthenic acid, an ammonium salt, or an acetylacetonate.

The catalyst according to the invention can also be chosen from commercially available products. For example, those from the ENGELHARD Company which proposes catalysts containing from 0.5 to 5% of ruthenium on aluminas or extruded charcoals can be used.

The catalytic hydrogenation according to the invention may be performed at a temperature ranging from 50° to 250° C., with a mole ratio hydrogen/perhaloethane (II) ranging from 0.5 to 4, under a pressure of 1 to 20 bars (preferably 1 to 5 bars) and an hourly flow rate of 1 to 20 moles of perhaloethane (II) per liter of catalyst.

EXAMPLES

The examples which follow illustrate the invention without limiting it. In Examples 2 to 4, the results are expressed as the overall degree of conversion ($DC_O$) and the selectivity (S) for a reaction product:

$$DC_O = 100 \times \frac{\text{Number of moles of compound (II) converted}}{\text{Number of moles of compound (II) introduced}}$$

$$S = 100 \times \frac{\text{Number of moles of product formed}}{\text{Number of moles of compound (II) converted}}$$

The analysis at admission to and emergence from the reactor being performed by on-line gas chromatography.

EXAMPLE 1 - Preparation of the catalysts

A rotary evaporator is charged with 50 ml (23 g) of an active charcoal having a porosity of 0.6 cm³/g and a specific surface area of 950 m²/g in extruded form 1.8 mm in diameter. After outgassing for 3 hours at 100° C. under reduced pressure (1 kPa), 70 ml of an aqueous solution of hydrated ruthenium trichloride $RuCl_3.xH_2O$ containing 1.5 g of ruthenium are introduced. The water is then evaporated off under reduced pressure (1 kPa). The residue is dried at 100° C. The latter is then treated at 400° C. for 2 hours under a stream of hydrogen (10 Nl/h). A catalyst containing 6% of ruthenium (catalyst A) is thereby obtained.

By working in the same manner but with an aqueous solution containing 0.12 g of ruthenium, a catalyst containing 0.5% of ruthenium (catalyst B) is obtained.

EXAMPLE 2

50 ml of the catalyst A described in Example 1 are introduced into an electrically heated Inconel tube 45 cm long and 2.72 cm in internal diameter. A mixture of hydrogen and 1,1-dichloro-1,2,2,2-tetrafluoroethane is then passed through the tube at the mole ratios, flow rates and temperatures shown in the following table. The last part of which collates the results obtained.

TABLE 1

| | TEST NO. | | | | |
|---|---|---|---|---|---|
| | 1 | 2 | 3 | 4 | 5 |
| Working Conditions: | | | | | |
| Temperature (°C.) | 150 | 200 | 200 | 200 | 200 |
| Mole ratio $H_2/C_2F_4Cl_2$ | 4 | 4 | 1 | 1 | 0.5 |
| Flow rate $C_2F_4Cl_2$ (mole/hour) | 0.07 | 0.07 | 0.18 | 0.08 | 0.10 |
| Results | | | | | |
| % $DC_O$ of $C_2F_4Cl_2$ | 43 | 91 | 40 | 56 | 33 |
| % S for $CF_3CHFCl$ | 49 | 82 | 84 | 87 | 88 |
| % S for $CF_3CH_3$ | 50 | 16 | 14 | 11 | 11 |

In most cases, the selectivity of the hydrogenolysis of a single C-Cl bond is greater than 80%.

By way of comparison, test nos. 1 and 2 were repeated, but with the catalyst A according to the invention replaced by a catalyst containing 5% of palladium prepared in the same manner and on the same support as in Example 1 with $PdCl_2$ instead of $RuC_3$. The results, collated in Table 2 below, show that, with this palladium catalyst, selectivity of the reaction is decidedly biased towards the abstraction of two chlorine atoms.

TABLE 2

| | COMPARATIVE TEST NO. | |
|---|---|---|
| | 6 | 7 |
| Working Conditions: | | |
| Temperature (°C.) | 150 | 200 |
| Mole ratio $H_2/C_2F_4Cl_2$ | 4 | 4 |
| Flow rate $C_2F_4Cl_2$ (mole/hour) | 0.07 | 0.07 |
| Results | | |
| % $DC_O$ of $C_2F_4Cl_2$ | 100 | 100 |
| % S for $CF_3CHFCl$ | 4 | 3 |
| % S for $CF_3CH_3$ | 1 | 1.2 |
| % S for $CF_3CH_2F$ | 94.5 | 95 |

EXAMPLE 3

50 ml of a fresh charge of catalyst A, on which various tests of hydrogenation of 1,1,1-trichloro-2,2,2-trifluoroethane ($CF_3$-$CCl_3$) are performed successively, are introduced into the same apparatus as in Example 2.

The working conditions for the tests and the results obtained are collated in Table 3 below. Besides the expected product, 1,1-dichloro-2,2,2-trifluoroethane ($CF_3CHCl_2$), 1,1,1-trifluoroethane ($CF_3CH_3$) is mainly found as a by-product and, in some cases, $C_4$ olefinic condensation products.

TABLE 3

| | WORKING CONDITIONS | | | RESULTS | | |
|---|---|---|---|---|---|---|
| Test No. | Temp °C. | Mole Ratio $H_2/C_2F_3Cl_3$ | $C_2F_3Cl_3$ Flow Rate (moles/h) | % $DC_O$ of $C_2F_3Cl_3$ | % S for $CF_3CHCl_2$ | % S for $CF_3CH_3$ |
| 11 | 50 | 0.83 | 0.12 | 10 | 100 | — |
| 12 | 100 | 0.83 | 0.12 | 28.5 | 94 | 4 |
| 13 | 110 | 0.83 | 0.12 | 42.5 | 89 | 3 |
| 14 | 150 | 1 | 0.10 | 70 | 77 | 3 |
| 15 | 170 | 0.90 | 0.14 | 74 | 79 | 4.5 |
| 16 | 200 | 0.83 | 0.12 | 68 | 59 | 3.5 |
| 17 | 115 | 0.56 | 0.19 | 59 | 63 | 1.6 |
| 18 | 100 | 0.91 | 0.14 | 64 | 79 | 2.1 |
| 19 | 100 | 1.6 | 0.096 | 80 | 80 | 3 |
| 20 | 100 | 3 | 0.093 | 55 | 80 | 4.2 |
| 21 | 150 | 3 | 0.093 | 87 | 53 | 8.3 |
| 22 | 100 | 3 | 0.058 | 59 | 92 | 6.3 |

EXAMPLE 4

In the same apparatus as in Example 2, and with a charge of 50 ml of catalyst, various tests of hydrogenolysis of 1,1,1-trichloro-2,2,2-trifluoroethane were performed using the following catalysts B, C and D:

B: catalyst containing 0.5% of Ru on charcoal, described in the last paragraph of Example 1, C: catalyst containing 1% of palladium on charcoal, prepared as in Example 1, but with $PdCl_2$ instead of $RuCl_3$, D: catalyst containing 5% of platinum on charcoal, prepared as in Example 1, but with $PtCl_6H_2$ instead of $RuCl_3$.

The working conditions and the results of these tests are collated in Table 4 below:

TABLE 4

| | TEST NO. | | | | | |
|---|---|---|---|---|---|---|
| | According to the invention | | Comparative | | | |
| | 31 | 32 | 33 | 34 | 35 | 36 |
| Working Conditions: | | | | | | |
| Catalyst | B | B | C | D | D | D |
| Temperature (°C.) | 200 | 150 | 150 | 80 | 100 | 125 |
| Mole ratio $H_2/C_2F_3Cl_3$ | 0.5 | 2.5 | 0.5 | 1.4 | 1.4 | 1.8 |
| Flow rate $C_2F_3Cl_3$ | 0.12 | 0.6 | 0.11 | 0.10 | 0.10 | 0.10 |

TABLE 4-continued

|  | \multicolumn{2}{c}{TEST NO.} | | | | |
|---|---|---|---|---|---|---|
|  | According to the invention | | Comparative | | | |
|  | 31 | 32 | 33 | 34 | 35 | 36 |
| (mole/hour) | | | | | | |
| Results | | | | | | |
| % DC$_O$ of C$_2$F$_3$Cl$_3$ | 21 | 6 | 18 | 92 | 93.5 | 100 |
| % S for CF$_3$CHCl$_2$ | 80 | 100 | 28 | 64 | 64 | 27 |
| % S for CF$_3$CH$_3$ | 0 | 0 | 72 | 32 | 34 | 48* |

*S for CF$_3$CHCl$_2$ = 20%

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. Process for preparing chlorofluoroethanes of the formula:

$$CF_3\text{-}CHF_xCl_{2-x} \quad (I)$$

where x is equal to 0 or 1, by the catalytic hydrogenation of a perhaloethane of the formula:

$$CF_3\text{-}CF_xCl_{3-x} \quad (II)$$

with hydrogen in the presence of a catalytically effective amount of a catalyst consisting of ruthenium deposited on a support.

2. The process according to claim 1, wherein the catalyst has a ruthenium content ranging from 0.1 to 10% by weight.

3. The process according to claim 2, wherein the concentration of the ruthenium is between 0.2 and 8%.

4. The process according to claim 1, wherein the support is an alumina, aluminum fluoride or an active charcoal.

5. The process according to claim 1, wherein the support is an active charcoal having a specific surface area between 200 and 1500 m$^2$/g, a porosity of 0.3 to 0.7 cm$^3$/g and a particle size of 1 to 10 mm.

6. The process according to claim 1, wherein the hydrogenation is performed at a temperature of between 50° and 250° C. and under a pressure of 1 to 20 bars.

7. The process according to claim 6, wherein the pressure is between 1 and 5 bars.

8. The process according to claim 1, wherein the mole ratio hydrogen/perhaloethane (II) is between 0.5 and 4.

9. The process according to claim 1, wherein the hourly flow rate of perhaloethane (II) is from 1 to 20 moles per liter of catalyst.

* * * * *